US012614628B2

(12) United States Patent
Danudibroto

(10) Patent No.: US 12,614,628 B2
(45) Date of Patent: Apr. 28, 2026

(54) METHOD FOR OBTAINING AN INDICATION ABOUT THE IMAGE QUALITY OF A DIGITAL IMAGE

(71) Applicant: AGFA NV, Mortsel (BE)

(72) Inventor: Adriyana Danudibroto, Mortsel (BE)

(73) Assignee: AGFA NV, Mortsel (BE)

( * ) Notice: Subject to any disclaimer, the term of this patent is extended or adjusted under 35 U.S.C. 154(b) by 565 days.

(21) Appl. No.: 18/080,886

(22) Filed: Dec. 14, 2022

(65) Prior Publication Data

US 2023/0197246 A1     Jun. 22, 2023

(30) Foreign Application Priority Data

Dec. 16, 2021     (EP) ..................................... 21214952

(51) Int. Cl.
*G06K 9/00*      (2022.01)
*G16H 30/20*      (2018.01)
*G16H 30/40*      (2018.01)

(52) U.S. Cl.
CPC ............. *G16H 30/20* (2018.01); *G16H 30/40* (2018.01)

(58) Field of Classification Search
CPC ........ G16H 30/20; G16H 30/40; A61B 6/469; A61B 6/505; A61B 6/5211; A61B 8/469; A61B 8/5215; G06T 7/70; G06T 7/0002; G06T 2207/10116; G06T 2207/20016; G06T 2207/20081; G06T 2207/20084; G06T 2207/30004; G06T 2207/30168
See application file for complete search history.

(56) References Cited

U.S. PATENT DOCUMENTS

| | | | |
|---|---|---|---|
| 10,593,041 B1 | 3/2020 | Shaw | |
| 10,799,189 B2 | 10/2020 | Nye et al. | |
| 2012/0269425 A1 * | 10/2012 | Marchesotti | ......... G06V 10/993 382/162 |
| 2022/0405916 A1 * | 12/2022 | Lu | ........................ G06V 10/776 |

FOREIGN PATENT DOCUMENTS

CN          112348059 A  *  2/2021

OTHER PUBLICATIONS

Mairhöfer et al., "An AI-based Framework for Diagnostic Quality Assessment of Ankle Radiographs," *Proceedings of Machine Learning Research*, 143: 484-496 (2021).
Tan et al., "EfficientDet: Scalable and Efficient Object Detection," Computer Vision Foundation, pp. 10781-10790 (2020).

* cited by examiner

*Primary Examiner* — Xin Jia
(74) *Attorney, Agent, or Firm* — Leydig, Voit & Mayer, Ltd.

(57) ABSTRACT

The invention relates to a method to give an indication about the image quality of a digital image in comparison to what the expected image quality in terms of image content and technical image quality parameters would be for a similar exposure type. The method evaluates whether parameters of the acquired image such as noise and dynamic range match the expectations for the intended exposure type, and whether certain regions of interest are present and properly presented in the image.

8 Claims, 2 Drawing Sheets

METHOD FOR OBTAINING AN INDICATION ABOUT THE IMAGE QUALITY OF A DIGITAL IMAGE

CROSS-REFERENCE TO RELATED APPLICATION

This patent application claims the priority of copending European Patent Application No. 21214952.0, filed Dec. 16, 2021, which is hereby incorporated by reference in its entirety.

TECHNICAL FIELD

The present invention relates the technical field of medical imaging. The invention relates to a method to validate the image quality of a digital image in comparison to what the expected image quality in terms of image content and technical image quality parameters would be for a similar exposure type. The method evaluates whether parameters of the acquired image such as noise and dynamic range match the expectations for the intended exposure type, and whether certain regions of interest are present and properly presented in the image.

BACKGROUND OF THE INVENTION

Standard X-ray projection radiography is the still one of the most important imaging modalities for diagnosis and treatment planning. In order to be able to perform these tasks, an adequate quality of the produced image is necessary.

In daily practice a first assessment of the overall quality of a radiograph is performed by the radiographer who acquires the image. But when subjected to time pressure or other circumstances, the radiographer may misjudge the image quality which may result in problems or disadvantages such as increased cost and unnecessary applied dose to the patient because of the need of a retake.

It therefore would be advantageous to setup an automated image quality assessment system to prevent these errors in a structural way. While it is relatively straightforward to judge at a glance on technical image quality parameters such as for instance the noise and contrast of an image, it takes more experience and time to judge on the image content quality of an image. The image content quality, being the presence and visibility of certain important anatomical features in the image.

As an example, a problem with the noise level, which may occur due to the application of too low dose in X-ray imaging or poor skin-transducer contact for ultrasound, can quickly be noticed by visual observation as the image will look incomprehensible, analogous to a photograph taken under poor lighting condition. In such a case, an image retake can be ordered and performed immediately. After all, the patient still is in the room. Alternatively, image enhancement software may still be able to salvage the image.

A radiograph may be of a perfect technical quality, and still may be worthless for diagnostic purposes if it suffers from poor image content quality, for instance in the case that the relevant structures would not be visible due to misalignment of the patient with the radiography system.

Problems with incorrect anatomical content of an image is more difficult to detect at a glance especially for the less experienced radiographer as the image appearance can still seem acceptable. It is often only after the referring clinician receives the image from the radiology department that such a problem is noticed. At that time, the patient will no longer be present for a retake of the image, which means that the patient has to be called back for a return to the radiology department, costing additional time and effort for all parties involved.

For some radiography examinations it may be vital that the image not only comprises a certain structure and a well-defined part of its surroundings, but also that the structure is correctly aligned or superimposed onto another one.

For an elbow exam in lateral projection, it is for instance required that the capitellum and trochlea are superimposed. At the same time the image should provide a clear profile view of the olecranon process, and the elbow joint should be open. The image also should provide a partial view of the humerus shaft in the field of view.

Similar lists of criteria can be defined for each acquisition type, such as for instance a thorax PA (posteroanterior projection), thorax lateral, shoulder AP (anteroposterior projection), abdomen AP, lumber spine lateral, knee AP, knee lateral, hand PA, hand lateral, foot AP, foot lateral, or alike.

The misalignment in an image is not easily measured, but the resulting image content quality may be easily assessed by an experienced radiologist.

The proposed invention tries to detect the presence of the required anatomical content in an image, and apply a score to the image quality content for the specific examination type. An automatic check can be done to see whether the image contains the correct and enough anatomical detail for the requested acquisition. For each acquisition, the presence of specific anatomical content can only be ensured when the patient is positioned correctly with respect to the X-ray source and the detector, and when the correct collimation is applied. Thus, the check should be done based on criteria that take these requirements into account.

While previous approaches to automate image quality evaluation already assess the technical image quality of an acquired image based on conventional computer vision methods, some approaches already try to take misalignment problems, such as incorrect collimation of the field of view, into account in order to assess the overall image quality.

One method described in the art that is based on deep-learning techniques uses a framework that is based on classification and segmentation neural networks (Mairhöfer, Dominik, et al. "An AI-based Framework for Diagnostic Quality Assessment of Ankle Radiographs." Medical Imaging with Deep Learning. 2021). In their work, a deep learning (DL) model is used to recognize the view of the X-ray image and based on the predicted view, another DL model is called to predict the criteria fulfilment. In total, three separate DL models were used only for assessing ankle radiographs: one for recognizing the view and detecting the region of interest (ROI) in the image, and one model each for anteroposterior (AP) and lateral view to assess the quality of the ankle radiograph. The limitation of this framework is that one framework can only be trained on a single acquisition type, such as for instance an ankle exposure.

The proposed invention in this application provides a deep-learning model that is more suitable compared to models described in the art, and overcomes the limitations mentioned above.

SUMMARY OF THE INVENTION

The present invention provides a method to provide an indication about image content quality of an acquired digital medical image, said indication being dependent on body part information and view position information associated with said image, comprising the steps of accessing said image at a computing device, obtaining body part information and view position information for said image, extracting multi-resolution features of various scale levels from said image by a trained deep learning backbone network that comprises multi-resolution convolutional layers, providing said multi-resolution features of various scale levels from said image and said body part and view position information as input for a trained feature combination network comprising bi-directional feature pyramid network layers that operate in both top-down and bottom-up direction, obtaining said indication about image content quality as an output result of an image quality head of said feature combination network, and wherein said backbone network and feature combination network are trained simultaneously.

In the context of the present invention the head comprises a convolutional layer or layers that process the combined features from the feature combination network. The output of the head will be the output of the Ai model.

In the context of the invention, the indication about the image content quality comes down to a score of the acceptability of the image content quality as it would be interpreted or evaluated by an experienced radiologist. This indication is in fact a prediction of the image content quality of an acquired image by the deep learning model of the invention. The score comes down to a value, where there are at least two possible outcomes: "acceptable" or "unacceptable". An alternative scoring could be a numerical scale (for instance, between 0 and 10, where 0 represents a very poor image content quality score, and 10 a perfect one).

Overall image quality refers to the combination of the technical image quality and the image content quality. The image content quality is however determined by the presence of the required anatomical content for the intended radiography study or examination type. The required anatomical content is thus different for each examination type.

The overall image quality in a clinical context is generally defined as the requirement from a clinician to visualize organs and structures with adequate contrast and critical reproduction of details, anatomical structures and edges.

The technical image quality may be evaluated by a number of objectively measurable parameters, such as for instance the spatial resolution, noise, image contrast, presence of artifacts and distortion. Some of these parameters are related to the quality of the imaging modality itself, others are related to the acquisition type and the physical constitution of the patient. Different exposure settings (kV, mAs) are applied for the same exposure type for patients with different physical constitutions.

The presence detection of anatomical content is performed in this invention by a particular deep learning model that is inspired by the EfficientDet object detector described by Tan et al. [Tan, Mingxing, Ruoming Pang, and Quoc V. Le. "Efficientdet: Scalable and efficient object detection." Proceedings of the IEEE/CVF conference on computer vision and pattern recognition. 2020.] that was designed to address the need for an object detector with computational efficiency and adaptability in mind. However architectural changes are proposed in order to overcome the limitation to train one model per pose or acquisition type, which intrinsically increases the requirement for memory significantly as more and more acquisition types are included in the system. Therefore, in the present invention a deep learning model is proposed that can perform different tasks (for instance: recognizing the view, recognizing the body part, indicating a ROI and evaluating the image content criteria fulfilment) for all acquisition types simultaneously.

Specific examples and preferred embodiments are set out in the dependent claims. Further advantages and embodiments of the present invention will become apparent from the following description and drawings.

DETAILED DESCRIPTION OF THE INVENTION

Figure 1:
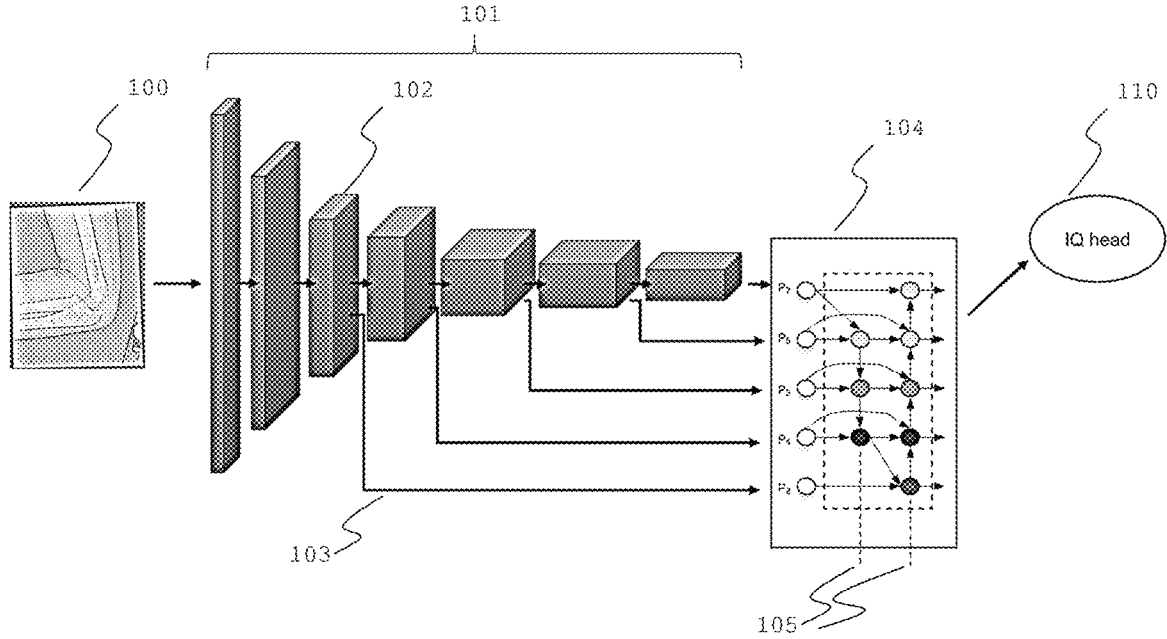
FIG. 1 gives a schematic overview of the deep learning model of the invention, depicting a backbone network [101] consisting of multi-resolution convolutional layers [102] and accepting the acquired medical image [100] as its input. The backbone network produces multi-resolution features [103], which are generated at different resolutions or scales of the original image, and feeding them into a feature combination network [104] comprising multi resolution feature combination layers [105]. The output head [110] performs the image quality assessment task, and produces the indication about the image content quality as an output result.

In the following detailed description, reference is made in sufficient detail to the above referenced drawings, allowing those skilled in the art to practice the embodiments explained below.

As one of the learnable parameters inside a neural network, a weight is by default initialized with a random number. For most image based tasks, the most popular initialization method is using model weights that are pre-trained with the ImageNet dataset for common object classification tasks. In general, this initialization gives better immediate results for this kind of classification tasks on images.

Lately, it has been noted that using the ImageNet pre-trained model for medical imaging task might result in suboptimal results due to the appearance differences between the photo image domain and the medical image domain. Thus, model pre-training with a self-supervised method with a high volume of unlabelled medical image data comes into the picture. For instance, an auto-encoder setup where the model output attempts to reconstruct the input image may be applied, as well as contrastive training where versions of the same input image and another input image are fed into the model to tell apart (or to contrast) between input that is from the same image and input that is not.

Model parameters can thus in principle be initialized randomly, by using an ImageNet dataset on a natural classification task, or by using a self-supervised method, such as an auto encoding task or through contrastive learning using an unlabeled relevant medical imaging dataset.

The design of the proposed deep learning network that is applied in the invention is a linear sequence of two deep learning models, of which the output of the first model feeds into the second model.

The first deep learning model is a so-called backbone network [101] consisting of multi-resolution convolutional layers [102] and accepts the acquired medical image [100] as its input. The backbone network produces multi-resolution features [103], which are generated at different resolutions or scales of the original image. The multi-resolution model eliminates the need to tradeoff between high-resolution and global context by using a cascade of low-resolution to high-resolution networks, and thus more efficiently yields features at the different scales.

The preferred backbone of the model is the so-called EfficientNet [Tan, Mingxing, and Quoc Le. "Efficientnet: Rethinking model scaling for convolutional neural networks." International Conference on Machine Learning. PMLR, 2019], which is a deep learning network that uses the compound scaling concept to adapt the models' width, depth and image resolution in a balanced way.

The extracted multi-resolution features [103] are fed into a second deep learning model, which is a so-called feature combination network [104] comprising multi resolution feature combination layers [105]. The feature combination network merges the features from various resolution/scale levels in both top-down and bottom-up directions.

The preferred feature network consists of bi-directional feature pyramidal network (BiFPN) layers [105] which is a compute-efficient way of combining the features in a top-down and bottom-up data flow. The connections are also designed in a regular pattern, making it more adaptable to new tasks instead of optimized for one specific task. The output head [110] is where the adaptation to the image quality assessment task happens. In the context of the invention, the network head always comprises an image quality head [110], optionally complemented with a body part head [111a] (for classification of the imaged body part), a view position head [111b] (classifying the view position of the imaged body part), a combination of both [111ab], or a bounding box head.

The difference with the state of the art lies in the choice of the output network head (the image quality head), and the appropriate training of the deep learning pipeline as a whole, wherein the backbone network and the feature combination network are trained simultaneously, wherein the first network passes on its output to the second network.

The different output heads define some of the different embodiments of the invention; where the network head is an image quality head, the output produced is the image quality content indicator as described above.

The training of the model requires the input of an appropriate set of labelled data, that comprise at least the acquired medical images that are labelled with the corresponding quality appreciation from experienced radiologists for the images. It is important to note that the training of the model does not have to be limited to a single acquisition type, which means that the same model can be trained on multiple acquisition types.

In a second embodiment, the deep learning model contains two output heads: the image quality head and a (combined) body part and view position head. The image quality head would give the prediction of how well the input image fulfills the image content quality criteria list for the requested body part and view position.

Figure 2:
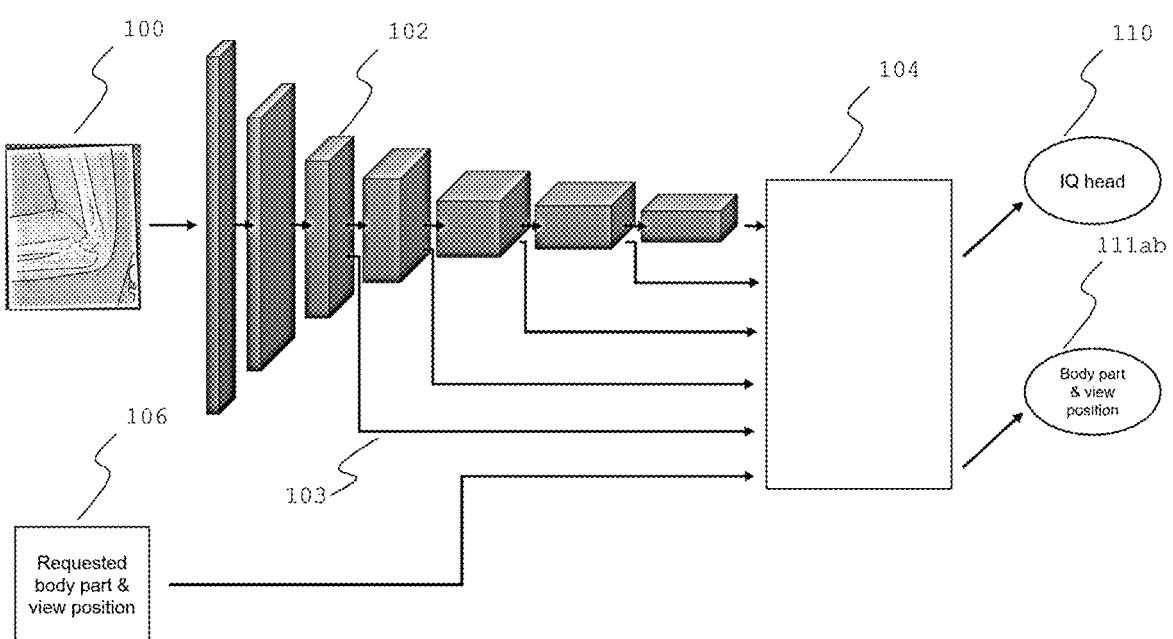
FIG. 2 gives a schematic overview of the deep learning model of the invention which comprises two output heads: an image quality head [110] and a (combined) body part and view position head [111*ab*]. Moreover, the requested body part and view position information is encoded and provided to the feature network as an additional input for the prediction [106].

The information about the requested body part and view position is encoded and provided to the feature network as an additional input for the prediction [106]. This data is obtained from either the order information relating to the requested acquisition, or from information that is stored together (for instance as a DICOM tag) with the image data file. The body part and view position is shown as one output head in FIG. 2, which means each specific patient pose is considered as one member of the class that is predicted by this network head. It means that one combination of body part/view position is considered as a single class of a potential prediction outcome.

Figure 3:
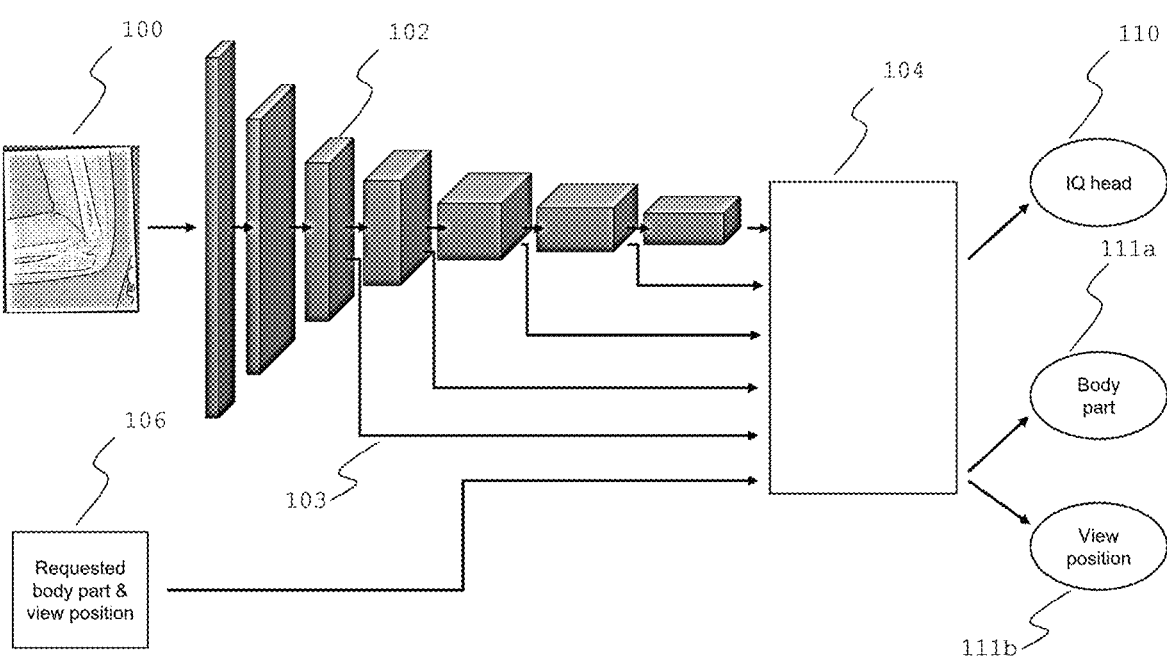
FIG. 3 gives a schematic overview of the deep learning model of the invention which comprises a separate body part head [111*a*] and view position head [111*b*] wherein each body part is considered as one class for the earlier head and each view position is considered as another class for the latter head.

In a third embodiment, a separate body part head and view position head can also be considered wherein each body part is considered as one class for this head and each view position is considered as another class for this head. (FIG. 3)

Figure 4:
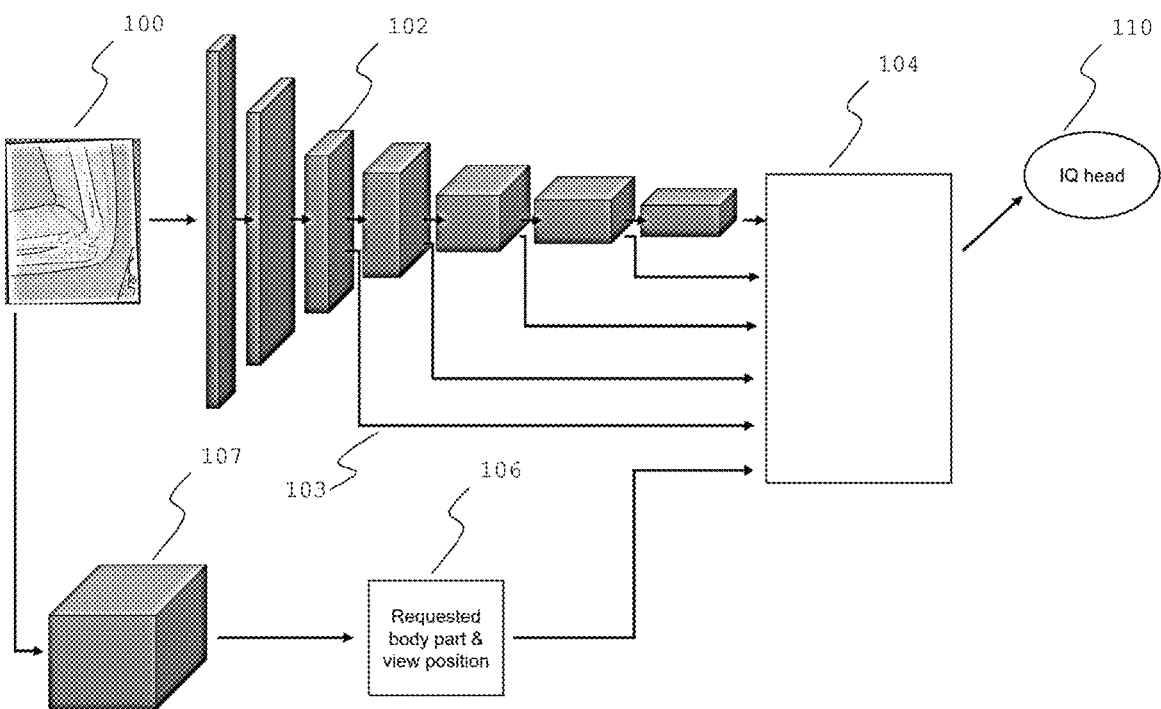
FIG. 4 gives a schematic overview of the deep learning model of the invention, wherein the information about the requested body part and view position is obtained from an additional deep learning model [107] that predicts the body part and view position [106] for input of the feature combination network [104].

In a fourth embodiment, the information about the requested body part and view position is obtained from an additional deep learning model [107] that predicts the body part and view position [106] rather than obtaining it from recorded information about the acquired image. This body part and view position information is then encoded, and is provided to the feature combination network of the main model as described earlier. (FIG. 4)

In yet another embodiment, a combination of output heads is provided where the content image quality, the body part and view position, and a bounding box containing the most significant region in the image or region of interest (ROI).

Similar to the first embodiment, the model takes the acquired X-ray image and the requested body part and view position information as input. In addition to the image quality head that provides the prediction of the image content quality criteria fulfillment for the requested body part, and the body part and view position head that provides the prediction of the body part and view position contained in the input image, the model has a bounding box head. The bounding box head gives the prediction about the location of the ROI containing the most significant region in the image that depicts the predicted body part and view position.

The invention claimed is:

1. A method of providing an indication about diagnostic image content quality of an acquired digital X-ray medical diagnostic image during an X-ray radiography acquisition workflow, as interpreted or evaluated by an experienced radiologist, said indication being dependent on body part information and view position information associated with said diagnostic image, the method comprising the steps of:

accessing said diagnostic image at a computing device, obtaining body part information and view position information for said diagnostic image, extracting multi-resolution features of various scale levels from said diagnostic image by a trained deep learning backbone network that comprises multi-resolution convolutional layers, providing said multi-resolution features of various scale levels from said diagnostic image and said body part and view position information as input for a trained feature combination network, and obtaining said indication about diagnostic image content quality as an output result of an image quality head of said trained feature combination network, wherein said backbone network and feature combination network are trained simultaneously, wherein the diagnostic image content quality indication is given by the image quality head as a score of each image content criteria acceptance level, wherein the diagnostic image content quality includes an assessment of anatomical structure alignment in the X-ray medical diagnostic image, and wherein the X-ray radiography acquisition workflow consists of a time during which a patient is in a radiology room.

2. The method of claim 1, wherein said body part information and view position information is obtained from an exam request that is associated with said diagnostic image and accessible from a radiology information system (RIS) on a computer device.

3. The method of claim 1, wherein said body part information and view position information is obtained from DICOM information stored with said diagnostic image.

4. The method of claim 1, wherein said body part information and view position information is obtained from a prediction of a trained deep learning model that receives said diagnostic image as an input.

5. The method of claim 1, wherein an additional network head of said feature combination network provides a prediction of said body part and view position associated with said diagnostic image.

6. The method of claim 1, wherein an additional network head of said feature combination network provides a prediction for a bounding box indicating a location of a region of interest associated with a body part of said diagnostic image.

7. The method of claim 1, wherein said backbone network and feature combination network are trained by supervised learning.

8. The method of claim 1, wherein said backbone network and feature combination network are trained by unsupervised learning.

* * * * *